United States Patent [19]

Gammer

[11] 4,072,800
[45] Feb. 7, 1978

[54] ELECTRIC STORAGE BATTERY ARRANGEMENT FOR USE IN ELECTRICALLY DRIVEN PROSTHETIC DEVICES

[75] Inventor: Peter Gammer, Duderstadt, Germany

[73] Assignee: Otto Bock Orthopädische Industrie K.G., Duderstadt, Germany

[21] Appl. No.: 725,192

[22] Filed: Sept. 21, 1976

[30] Foreign Application Priority Data

Sept. 26, 1975 Germany .............................. 2542933

[51] Int. Cl.² .............................................. H01M 2/10
[52] U.S. Cl. ......................................... 429/97; 429/98
[58] Field of Search ....................... 429/100, 96, 98, 97

[56] References Cited

U.S. PATENT DOCUMENTS

| | | | |
|---|---|---|---|
| 2,589,071 | 3/1952 | Galasso | 429/98 |
| 3,301,712 | 1/1967 | Bach | 429/100 |
| 3,445,297 | 5/1969 | Sidell | 429/98 |
| 3,742,832 | 7/1973 | Stoneham | 429/98 |

FOREIGN PATENT DOCUMENTS 959,541   12/1974   Canada ................................. 429/100

Primary Examiner—Donald L. Walton
Attorney, Agent, or Firm—Michael J. Striker

[57] ABSTRACT

An electric storage battery arrangement includes a frame which is to be mounted in the prosthetic device, and a storage battery which is insertable into the frame. A snap-holding arrangement holds the storage battery in the frame and includes a lever pivotable in the frame between a releasing and a holding position, being biased toward the releasing position and having one arm that holds the storage battery in the frame. Electric contacts are mounted on the lever, such contacts being arranged in the electric circuit of the drive of the prosthetic device and being in an electric contact with the terminals of the storage battery when the latter is fully inserted in the frame. The lever has a pair of cylindrical projections received in a depression of the frame and held therein against displacement other than pivoting by an arresting member connected to the frame. The storage battery has a centering recess intermediate the terminals, and another recess at the end spaced from the terminals, and a centering projection of the lever, and another projection of the frame, are received therein when the battery is at least partly inserted into the frame. A pressing member is urged into contact with the centering projection when received in the centering recess.

15 Claims, 5 Drawing Figures

ELECTRIC STORAGE BATTERY ARRANGEMENT FOR USE IN ELECTRICALLY DRIVEN PROSTHETIC DEVICES

BACKGROUND OF THE INVENTION

The present invention relates to electric storage battery arrangements in general, and more particularly to an arrangement of this type which can be used in electrically driven prosthetic devices.

There are already known various electrically driven prosthetic devices which are controlled by myoelectric or electro-mechanical control systems, such prosthetic devices being driven by electric power derived from a storage battery which is accommodated within the prosthetic device. Such prosthetic devices are discussed for instance, in the periodical called Medizinische Technik, December 1970, pages 393 to 394. However, experience obtained in connection with the use of these prosthetic devices has revealed that the electric storage battery arrangements used therein leave much to be desired.

SUMMARY OF THE INVENTION

It is a general object of the present invention to avoid the disadvantages of the prior art electric storage battery arrangements.

More particularly, it is an object of the present invention to provide a rechargeable electric storage battery arrangement which is simple in construction and reliable in operation.

A further object of the present invention is to provide a storage battery arrangement which is perfectly suited for use in electrically driven prosthetic devices.

A concomitant object of the present invention is to so construct the storage battery arrangement that it can be easily integrated into prosthetic devices of various shapes and dimensions.

A still other object of the present invention is to devise an electric storage battery arrangement in which the storage battery proper can be easily inserted and/or replaced.

A yet further object of the present invention is to provide an electric storage battery arrangement which has relatively small dimensions, particularly transverse dimensions, so as to render possible use of such arrangements even in relatively long but narrow prosthetic devices.

In pursuance of these objects and others which will become apparent hereafter, one feature of the present invention resides, briefly stated, in an electric storage battery arrangement for use in a prosthetic device of the type having an electric drive and an electric circuit for the same, in a combination which comprises a mounting frame adapted to be mounted on the prosthetic device; a storage battery interchangeably insertable into the mounting frame and having a pair of electric terminals; and a pair of electric contacts arranged in the electric circuit of the electric drive and in respective contact with the electric terminals of the storage battery when the latter is inserted into the mounting frame. The electric contacts are mounted on the mounting frame, or on a lever pivotally mounted on the mounting frame.

The mounting frame may be fitted in a tensionless manner in a body of the prosthetic device, which is made of, for instance, hardenable resin. The mounting frame may then be rigidly connected to the body of the prosthetic device, for example, by using a sealing resin.

Inasmuch as the electric contacts are provided either directly on the mounting frame or on the above-mentioned lever which only pivots relative to the mounting frame but is not intended to be removed therefrom, no connecting wires need be provided on the electric storage battery proper, particularly in view of the fact that the electric contact between the electric contacts and the electric terminals is established by merely inserting the electric storage battery into the mounting frame. Not only the insertion, but also the replacement of the storage battery, consequently, is especially simple. In view of this simplicity of replacement, the storage battery can have a storage capacity which is sufficient for powering the prosthetic device for about one day, and the exhausted storage battery can be replaced by a fresh one either in the evening or, when the power demand is greater, even during the day, by the user of the prosthetic device. The electric contacts of the mounting frame, contacting the electric terminals of the storage battery, automatically establish the proper connection for the supply of electric current to the drive of the electrically driven prosthetic device upon the insertion of the electric storage battery into the mounting frame.

In a currently preferred embodiment of the present invention, the electrical terminals are configurated with respective slots, and the electric contacts are constructed as contact blades which are receivable in the respective slots for establishing electric contact with the electric terminals. When the terminals and contacts are configurated in the above-mentioned way, the contact blades of the mounting frame slide easily and reliably into the respective slots of the electric terminals of the storage battery.

According to a further concept of the present invention, the storage battery is held in the mounting frame, upon insertion thereinto, by means of a snapaction holding arrangement. The holding arrangement preferably includes a lever mounted on the mounting frame for pivoting between a releasing position for insertion and withdrawal of the storage battery and a holding position for holding the storage battery in the mounting frame upon insertion, the lever including one arm which abuts against the inserted storage battery in the holding position of the lever. The lever may also have another arm, and a biasing means, such as a spring, may extend between the mounting frame or a part connected thereto and such arm for urging the lever toward the releasing position thereof. A simple pivoting of the lever towards its releasing position results in releasing the storage battery from the mounting frame so that the storage battery can be withdrawn from the mounting frame. The provision of the contacts or contact blades directly on the lever facilitates the introduction into and cooperation with the terminals of the storage battery.

A very good retention of the inserted storage battery in the mounting frame is assured when a connecting recess is provided on the storage battery opposite to the terminals and a connecting projection is provided on the longitudinal end of the mounting frame which is spaced from the lever, the connecting projection being received in the connecting recess when the storage battery is at least partly inserted into the mounting frame.

In an especially simple embodiment which can be extremely well manufactured by using injection-molded synthetic plastic parts, the mounting frame is formed with a depression, and the lever has a pair of cylindrical projections laterally thereof, the projections being receivable in the depression of the mounting frame and mounting the lever therein for pivoting between the releasing and holding positions thereof. In this embodiment, an arresting insert may be provided which is mounted on the mounting frame and which is operative for arresting the cylindrical projections in the depression against all movement but the pivoting. In this embodiment, the biasing means which urges the lever toward the releasing position thereof may include an annular spring partly accommodated in a groove of the arresting insert.

A particularly simple exchange of the storage battery is assured when the storage battery has a centering recess intermediate the electric terminals thereof, and when the lever has a centering projection intermediate the electric contacts and receivable in the centering recess when the storage battery is at least partly inserted into the mounting frame. In this embodiment, a pressing member may be mounted in the storage battery for displacement between an extended position in the centering recess and a retracted position out of the same, biasing means, such as a spring, being provided in the storage battery, which urges the pressing member toward the extended position thereof and against the centering projection of the lever when such centering projection is received in the centering recess. When the arrangement is constructed in the above-discussed way, and the lever is pivoted into its releasing position in which the above-mentioned one arm of the lever raises the storage battery, then the spring acting on the pressing member will automatically eject the storage battery out of the mounting frame so that the user of the prosthetic device may remove such storage battery, even using a prosthetic hand.

As currently preferred, the length of the storage battery may be approximately three times the width thereof, and the mounting frame may have a tub-shaped configuration having an open side through which the storage battery is insertable into the tub-shaped mounting frame.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DETAILED DISCUSSION OF THE PREFERRED EMBODIMENTS

Figure 1:
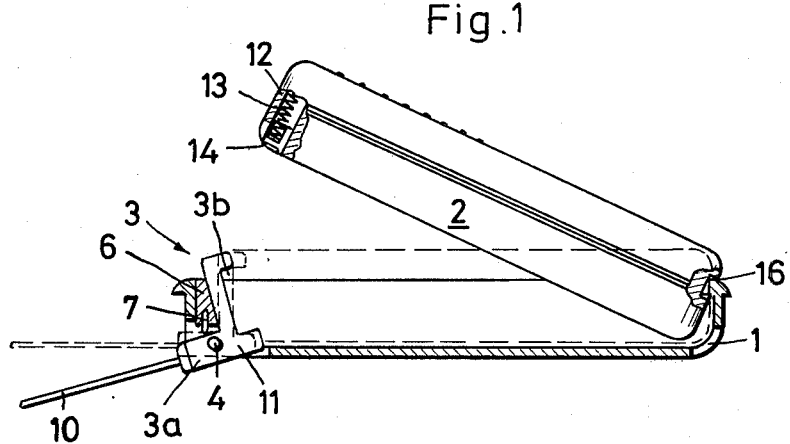
FIG. 1 is a longitudinal sectional view of a mounting frame with a storage battery received therein.
Figure 2:
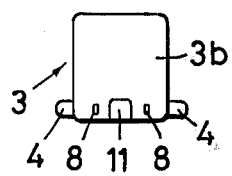
FIG. 2 is a front view of a lever to be used as a snap-action holding arrangement in the mounting frame of FIG. 1.
Figure 3:
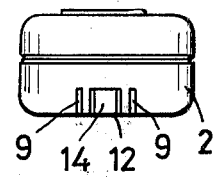
FIG. 3 is a front elevational view of a storage battery compatible with the mounting frame of FIG. 1.
Figure 4:
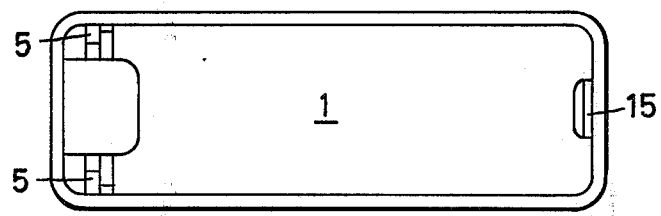
FIG. 4 is a top plan view of the mounting frame of FIG. 1.
Figure 5:
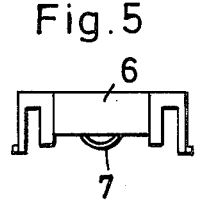
FIG. 5 is a side elevational view of an arresting insert for use in the mounting frame of FIG. 1.

Referring now to the drawings, and first to FIG. 1 thereof, it may be seen therein that the electric storage battery arrangement of the present invention includes a mounting frame 1 which is adapted to receive a storage battery 2. When fully inserted, the storage battery 2 assumes the position which is illustrated in FIG. 1 in dashed lines.

The storage battery 2 is held in the mounting frame 1 by means of a snap-action holding arrangement. This holding arrangement consists of, in the first place, a lever 3 pivotally mounted in the mounting frame 1 and having a shorter arm 3a and a longer arm 3b, the latter having a jaw-like configuration and straddling one longitudinal end of the inserted storage battery 2. The lever 3 is mounted in the mounting frame 1 for pivoting between a holding position, shown in dashed lines, and a releasing position shown in full lines in FIG. 1, with the storage battery being shown in full lines in FIG. 1 in a position corresponding to the releasing position of the lever 3.

At each side of the lever 3, there is provided a cylindrical projection or nose 4, the projections 4 defining the pivoting axis of the lever 3 with one another, and being received in a depression 5 provided in the holding frame 1. The lever 3 is arrested in the depression 5 against any other displacement but the pivoting between the releasing and holding positions by means of an arresting member 6 which is slidingly introduced into the mounting frame 1. An annular spring 7 is partly received in a groove provided in the arresting insert 6, the annular spring 7 pressing against the shorter arm 3a of the lever 3 and urging the latter toward the releasing position thereof.

A pair of contacts 8, constructed as contact blades, is mounted on the lever 3, which contacts 8 cooperate with the electric terminals 9 of the storage battery 2 when the latter is inserted into the mounting frame 1. The terminals 9 can be so constructed as to define a slot in each of the terminals, and the contact blades are then received in the respective slots of the respective terminals 9 when the storage battery 2 is fully received in the mounting frame 1.

The contacts 8 are each electrically connected to one wire of a connecting electric cable 10. A centering projection 11 is provided on the lever 3 intermediate the contacts 8, which centering projection 11 is received in a centering recess 12 of the storage battery 2 when the latter is received in the mounting frame 1. A pressure member 14 is mounted in the storage battery 2 for movement between a retracted position outside of, and an extended position within, the centering recess 12, and a spring 13 urges the pressing member 14 towards its extended position so that the latter is urged against the centering projection 11 of the lever 3 when the centering projection 11 is received within the centering recess 12.

The mounting frame 1 is provided, at its longitudinal end which is spaced from the longitudinal end at which the lever 3 is mounted, with a projection 15 which is received in a recess 16 of the storage battery 12 when the latter is received in the mounting frame 1. The storage battery 2 is of an approximately rectangular shape, the length of the storage battery 2 being approximately three times the width of the storage battery 2. The mounting frame 1, as illustrated, is constructed to be of a tub-shaped configuration, having an open end or side which faces toward the exterior of the prosthetic device. The various components of the electric storage battery arrangement are preferably made of synthetic plastic material, which simplifies their manufacture and facilitates their assembly.

FIGS. 2 to 5 illustrate some details of the electric storage battery arrangement of the present invention, particularly of the storage battery 2, the lever 3 and the arresting insert 6, which details have already been discussed above.

When the storage battery 2, preferably of the rechargeable type, is to be inserted into the mounting frame 1, the storage battery 2 is first so introduced into the mounting frame 1 that the projection 15 of the mounting frame 1 enters the recess 16 of the storage battery 2. After that, pressure is exerted upon the partly inserted storage battery 2 which results in a movement of the lever 3 from the releasing position into the holding position. Because of the provision of the contacts 8 directly on the lever 3, their electric connection with the electric terminals 9 of the storage battery 2 is established at the same time.

On the other hand, when the lever 3 is pivoted towards its releasing position, it releases the storage battery 2 and the spring 13 lifts the storage battery 2 to such an extent that it can be simply and safely removed from the mounting frame 1, particularly since the contacts 8 have been removed from the terminals 9 during the pivoting of the lever 3 toward the releasing position thereof.

It will be understood that each of the elements described above or two or more together, may also find a useful application in other types of constructions differing from the types described above.

While the invention has been illustrated and described as embodied in an electric storage battery arrangement for use in electrically driven prosthetic devices, it is not intended to be limited for the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An electric storage battery arrangement for use in a prosthetic device of the type having an electric drive and an electric circuit for the same, comprising, in combination, a mounting frame adapted to be mounted on the prosthetic device; a storage battery interchangeably insertable into said mounting frame and having a pair of electric terminals configured with respective slots; and a pair of electric contacts arranged in the electric circuit and constructed as contact blades receivable in said respective slots for establishing electric contact with said electric terminals of said storage battery when the latter is inserted into said mounting frame.

2. A combination as defined in claim 1, wherein said electric contacts are mounted on said mounting frame upon mounting of the latter on the prosthetic device.

3. A combination as defined in claim 1; and further comprising a snap-action holding arrangement for holding said storage battery in said mounting frame upon insertion thereinto.

4. A combination as defined in claim 3, wherein said holding arrangement includes a lever mounted on said mounting frame for pivoting between a releasing position for insertion and withdrawal of said storage battery, and a holding position for holding said storage battery in said mounting frame upon insertion, said lever including one arm which abuts against said inserted storage battery in said holding position of said lever.

5. A combination as defined in claim 4, wherein said lever also has another arm; and further comprising biasing means extending between said mounting frame and said lever and urging the latter toward said releasing position thereof.

6. A combination as defined in claim 4, wherein said mounting frame has a depression; and wherein said lever has a pair of cylindrical projections laterally thereof, said projections being receivable in said depression and mounting said lever for pivoting between said releasing and holding positions thereof.

7. A combination as defined in claim 6, and further comprising an arresting insert mounted on said mounting frame and operative for arresting said cylindrical projections in said depression against all movement but said pivoting.

8. A combination as defined in claim 7; and further comprising biasing means arranged between said arresting insert and said lever and urging the latter toward said releasing position thereof.

9. A combination as defined in claim 8, wherein said arresting insert includes a groove; and wherein said biasing means includes an annular spring partly accommodated in said groove of said arresting insert.

10. A combination as defined in claim 4, wherein said mounting frame is elongated and said lever is mounted at one longitudinal end thereof; and further comprising a connecting recess on said storage battery and a connecting projection on the other longitudinal end of said mounting frame and received in said connecting recess when said storage battery is at least partly inserted into said mounting frame.

11. A combination as defined in claim 1, wherein said storage battery has a length and a width; and wherein said length is approximately three times said width.

12. A combination as defined in claim 1, wherein said mounting frame has a tub-shaped configuration and has an open side through which said storage battery is insertable into said mounting frame.

13. An electric storage battery arrangement for use in a prosthetic device of the type having an electric drive and an electric circuit for the same, comprising, in combination, a mounting frame adapted to be mounted on the prosthetic device; a storage battery interchangeably insertable into said mounting frame and having a pair of electric terminals; a snap-action holding arrangement for holding said storage battery in said mounting frame upon insertion thereinto, including a lever mounted on said mounting frame for pivoting between a releasing position for insertion and withdrawal of said storage battery, and a holding position for holding said storage battery in said mounting frame upon insertion, said lever including one arm which abuts against said inserted storage battery in said holding position of said lever; and a pair of electric contacts mounted on said lever and arranged in the electric circuit and in respective contact with said electric terminals of said storage battery when the latter is inserted into said mounting frame.

14. A combination as defined in claim 13, wherein said storage battery has a centering recess intermediate said electric terminals thereof; and wherein said lever has a centering projection intermediate said electric contacts and received in said centering recess when said storage battery is at least partly inserted into said mounting frame.

15. A combination as defined in claim 14, and further comprising a pressing member mounted in said storage battery for displacement between an extended position in said centering recess and a retracted position out of the same; and biasing means urging said pressing member toward said extended position thereof and against said centering projection when the latter is received in said centering recess.

* * * * *